(12) United States Patent
Chen

(10) Patent No.: US 12,377,285 B2
(45) Date of Patent: Aug. 5, 2025

(54) METHOD AND APPARATUS FOR CYCLO-SCANNER USING SURFACE EMITTING LASERS OR LEDs

(71) Applicant: Iridex Corporation, Mountain View, CA (US)

(72) Inventor: Howard Chen, San Jose, CA (US)

(73) Assignee: IRIDEX Corporation, Mountain View, CA (US)

( * ) Notice: Subject to any disclaimer, the term of this patent is extended or adjusted under 35 U.S.C. 154(b) by 939 days.

(21) Appl. No.: 17/346,740

(22) Filed: Jun. 14, 2021

(65) Prior Publication Data

US 2021/0299466 A1    Sep. 30, 2021

Related U.S. Application Data

(62) Division of application No. 15/892,809, filed on Feb. 9, 2018, now Pat. No. 11,058,890.

(Continued)

(51) Int. Cl.
*A61N 5/06*    (2006.01)
*A61B 3/14*    (2006.01)
(Continued)

(52) U.S. Cl.
CPC .............. *A61N 5/0622* (2013.01); *A61B 3/14* (2013.01); *A61F 9/00821* (2013.01); *A61F 9/009* (2013.01); *A61B 2017/00057* (2013.01); *A61B 2017/00734* (2013.01); *A61B 2018/00702* (2013.01); *A61F 2009/00844* (2013.01); *A61F 2009/00868* (2013.01);
(Continued)

(58) Field of Classification Search
CPC ................. A61N 5/0622; A61N 5/067; A61N 2005/0626; A61N 2005/0629; A61N 2005/0644; A61N 2005/0648; A61N 2005/0652; A61F 9/009; A61F 2009/00821; A61F 2009/00844; A61F 2009/00868; A61F 2009/00891; A61B 3/14
USPC .......................................................... 607/89
See application file for complete search history.

(56) References Cited

U.S. PATENT DOCUMENTS 3,034,403 A    5/1962 Neefe
4,576,453 A    3/1986 Borowsky
(Continued)

FOREIGN PATENT DOCUMENTS

CN    1714740    1/2006
CN    102143725    8/2011
(Continued)

*Primary Examiner* — Ahmed M Farah
(74) *Attorney, Agent, or Firm* — Kilpatrick Townsend & Stockton LLP

(57) ABSTRACT

A handheld device for delivering therapeutic light toward an eye of a patient includes a device housing that is configured to be held by a user in delivering the therapeutic light, a plurality of light sources disposed within the device housing, and an array of lenses disposed near the distal end of the device housing. Each light source is configured to independently emit a beam of therapeutic light and each lens of the array is aligned with a respective light source so that each beam of therapeutic light that is emitted from the respective light sources is focused and directed by the respective lenses of the array to target tissue of the eye in order to therapeutically treat to the target tissue.

26 Claims, 5 Drawing Sheets

Related U.S. Application Data

(60) Provisional application No. 62/459,487, filed on Feb. 15, 2017.

(51) Int. Cl.
*A61F 9/008* (2006.01)
*A61F 9/009* (2006.01)
*A61B 17/00* (2006.01)
*A61B 18/00* (2006.01)
*A61N 5/067* (2006.01)

(52) U.S. Cl.
CPC .............. *A61F 2009/00891* (2013.01); *A61N 2005/0629* (2013.01); *A61N 2005/0644* (2013.01); *A61N 2005/0648* (2013.01); *A61N 2005/0652* (2013.01); *A61N 5/067* (2021.08)

(56) References Cited

U.S. PATENT DOCUMENTS

| | | |
|---|---|---|
| 4,732,148 A | 3/1988 | L'Esperance, Jr. |
| 4,732,715 A | 3/1988 | Bawa et al. |
| 4,856,513 A | 8/1989 | Muller |
| 4,966,452 A | 10/1990 | Shields et al. |
| 5,108,388 A | 4/1992 | Trokel |
| 5,135,466 A | 8/1992 | Fedorov et al. |
| 5,147,284 A | 9/1992 | Fedorov et al. |
| 5,152,759 A | 10/1992 | Parel |
| 5,376,086 A | 12/1994 | Khoobehi et al. |
| 5,434,630 A | 7/1995 | Bransome |
| 5,697,923 A | 12/1997 | Poler |
| 5,719,656 A | 2/1998 | Bowling |
| 6,059,775 A | 5/2000 | Nielsen |
| 6,520,956 B1 | 2/2003 | Huang |
| 6,554,424 B1 | 4/2003 | Miller et al. |
| 6,874,886 B2 | 4/2005 | Miller et al. |
| 7,321,795 B2 | 1/2008 | Bogdanowicz |
| 7,564,014 B2 | 7/2009 | Huh |
| 7,727,138 B2 | 6/2010 | Alvarado |
| 8,070,688 B2 | 12/2011 | Livne et al. |
| 8,287,592 B2 | 10/2012 | Silvestrini |
| 8,308,292 B2 | 11/2012 | Arai et al. |
| 8,527,055 B2 | 9/2013 | Rickard |
| 8,914,089 B2 | 12/2014 | Abreu |
| 9,138,142 B2 | 9/2015 | Christie et al. |
| 9,144,376 B2 | 9/2015 | Guth et al. |
| 11,020,612 B2 | 6/2021 | Chen |
| 11,058,890 B2* | 7/2021 | Chen .................... A61B 3/14 |
| 11,576,569 B2* | 2/2023 | Chen .................... A61B 18/22 |
| 2003/0109907 A1 | 6/2003 | Shadduck |
| 2004/0043351 A1 | 3/2004 | Logan et al. |
| 2005/0003322 A1* | 1/2005 | Logan ................ A61C 19/004 |
| | | 433/29 |
| 2005/0033420 A1 | 2/2005 | Christie et al. |
| 2005/0046794 A1 | 3/2005 | Silvestrini et al. |
| 2006/0271026 A1 | 11/2006 | Silvestrini et al. |
| 2010/0076419 A1 | 3/2010 | Chew et al. |
| 2011/0137303 A1* | 6/2011 | Dolleris ............... A61N 5/0616 |
| | | 606/17 |
| 2011/0137307 A1 | 6/2011 | Imran |
| 2012/0209356 A1 | 8/2012 | Eckhouse et al. |
| 2012/0226268 A1* | 9/2012 | Liu ..................... A61N 5/0613 |
| | | 606/9 |
| 2012/0283557 A1 | 11/2012 | Berlin |
| 2013/0060306 A1 | 3/2013 | Colbauch |
| 2013/0123761 A1 | 5/2013 | Belkin et al. |
| 2014/0192311 A1 | 7/2014 | Pletcher et al. |
| 2015/0238357 A1 | 8/2015 | Goldberg et al. |
| 2015/0366706 A1 | 12/2015 | Belkin et al. |
| 2015/0374539 A1 | 12/2015 | Buzawa et al. |
| 2016/0192988 A1 | 7/2016 | Albright |
| 2017/0007834 A1 | 1/2017 | Irazoqui et al. |
| 2017/0087014 A1 | 3/2017 | Potter, Jr. et al. |
| 2018/0000337 A1* | 1/2018 | Chen .................... A61B 3/0008 |
| 2019/0099291 A1 | 4/2019 | Herekar |
| 2019/0232078 A1 | 8/2019 | Tai |

FOREIGN PATENT DOCUMENTS

| | | |
|---|---|---|
| CN | 105877974 | 8/2016 |
| DE | 3535072 | 4/1987 |
| IL | 129227 | 2/2000 |
| JP | 2008518683 | 6/2008 |
| JP | 2013518672 | 5/2013 |
| JP | 2016507321 | 3/2016 |
| KR | 200440586 | 6/2008 |
| WO | 0057773 | 10/2000 |

\* cited by examiner

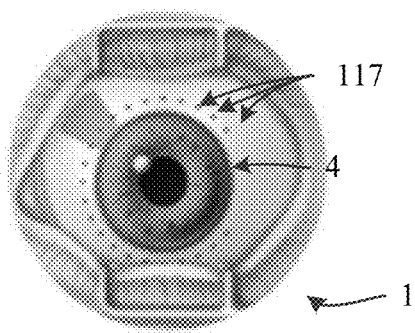
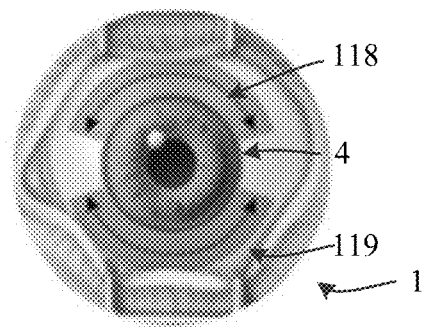
Figure 6                               Figure 7
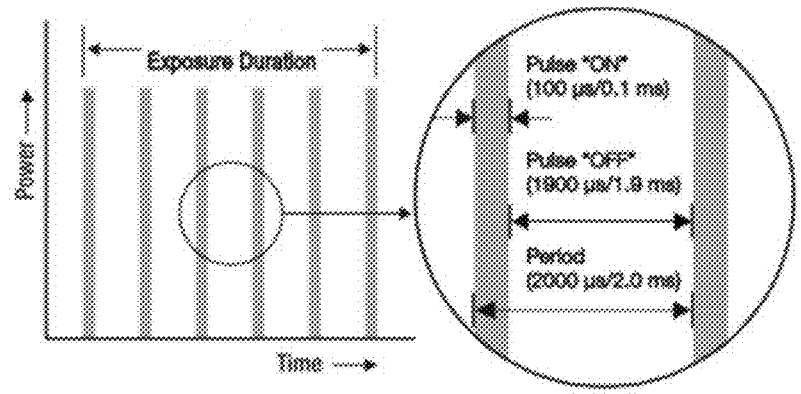
Figure 8
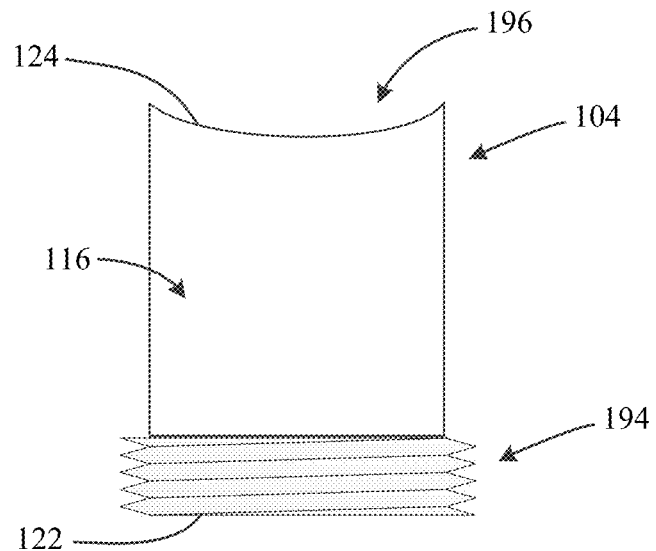
Figure 9

METHOD AND APPARATUS FOR CYCLO-SCANNER USING SURFACE EMITTING LASERS OR LEDs

CROSS-REFERENCE TO RELATED APPLICATIONS

This Application is a divisional of U.S. patent application Ser. No. 15/892,809 filed Feb. 9, 2018, which claims priority to Provisional U.S. Patent Application No. 62/459,487 filed Feb. 15, 2017, entitled "Method and Apparatus for Cyclo-Scanner Using Surface Emitting Lasers or LEDs," the entire disclosure of which are hereby incorporated by reference, for all purposes, as if fully set forth herein. This Application is also related to Provisional U.S. Patent Application No. 62/459,466 filed Feb. 15, 2017, entitled "Method and Eye Mask Apparatus for Treating an Eye Using a Broad Area Light Source," Provisional U.S. Patent Application No. 62/516,478 filed Jun. 7, 2017, entitled "Method and Eye Mask Apparatus for Treating an Eye Using a Broad Area Light Source," and U.S. patent application Ser. No. 15/892,893 filed Feb. 9, 2018, now U.S. Pat. No. 11,020,612. The entire contents of all aforementioned U.S. Patent Applications are hereby incorporated by reference, for all purposes, as if fully set forth herein.

BACKGROUND OF THE DISCLOSURE

The present disclosure is generally related to medical systems, devices, and methods for treating a glaucomatous eye. Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Elevated intraocular pressure (IOP) is a significant risk factor for developing glaucoma. IOP is a function of production of aqueous humor by the ciliary body of the eye and its drainage through the trabecular meshwork and all other outflow pathways including the uveoscleral pathway. Aqueous humor is a complex mixture of electrolytes, organics solutes, and other proteins that supply nutrients to the non-vascularized tissues of the anterior chamber of the eye. It flows from the ciliary bodies into the posterior chamber, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber via Schlemm's canal into scleral plexuses and the general blood circulation. In open angle glaucoma there is reduced flow through the trabecular meshwork. In angle closure glaucoma, the iris is pushed forward against the trabecular meshwork, preventing the egress of fluid.

Uveoscleral outflow is a non-conventional pathway that is gaining importance in the management of glaucoma. In uveoscleral outflow, aqueous humor enters the ciliary muscles from the anterior chamber and exits through the supraciliary space and across the anterior or posterior sclera. Uveoscleral outflow may contribute significantly to total aqueous humor outflow.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are expensive and have undesirable side effects, which can cause compliance-dependent problems over time.

Surgery may also be used to increase the outflow or to lower the production of aqueous humor. Laser trabeculoplasty is the application of a laser beam over areas of the trabecular meshwork to increase the outflow. Cyclocryotherapy and laser cyclophotocoagulation are surgical attempts to lower the production of aqueous humor by the ciliary processes. Although they may be effective, these destructive surgical interventions are normally used as a last resource in the management of glaucoma due to the risk of the severe complication of phthisis bulbi. Other adverse side effects of cyclodestructive surgical procedures may include ocular hypotony and inflammation of the anterior eye segment, which may be associated with an increased incidence of macula complications. Still other adverse side effects include transient hyphaema and exudates in the anterior chamber, uveitis, visual loss, and necrotizing scleritis.

In laser transscleral cyclophotocoagulation, high intensity continuous wave (CW) infrared laser energy is directed through selected portions of the pars *plicata* region to the ciliary body, structures under the scleral layers and the overlying conjunctiva. Selected portions of the ciliary body and related processes are permanently destroyed, thereby decreasing the overall production of aqueous humor. Laser energy may be directed through air to a patient seated at a special slit lamp. Alternatively, laser energy may be delivered through the use of fiber optic handpieces placed in contact with the patient's eyeball. In both laser energy delivery methods, however, accurately and repeatedly directing a laser beam to a subsurface non-visible target such as the ciliary body can be challenging for a surgeon.

Conventional laser based surgical system use a single light source such as an edge emitting diode laser, diode pumped solid state laser, or fiber laser to treat glaucoma conditions. In this conventional systems, the light from a laser is transported by an optical waveguide (e.g., multimode fiber probe) to the site of the treatment in an eye. The probe used for glaucoma treatment typically touches the surface of the eye, with the laser source releasing pulsed energy at a target or treatment spot. The probe is then moved to a different target or treatment spot, typically in a clockwise or counterclockwise rotation around the edge of the eye, and the probe is then used again to release pulsed energy at the new target or treatment spot. This process is commonly referred to as "cyclophotocoagulation" for treating an eye.

SUMMARY OF THE DISCLOSURE

Embodiments of the present disclosure generally relate to ophthalmic laser treatment systems. In some embodiments, the ophthalmic laser treatment systems may include a handheld single use treatment device that includes an array of lenses that are employed to deliver therapeutic light to target tissue of the eye to treat various conditions, such as glaucoma. For example, in certain embodiments, the treatment device may be provided for cyclophotocoagulation of the eye.

The handheld treatment device described herein provides several advantages over conventional systems including the use of multiple independent light sources and lenses rather than a single light source and lens system. The use of the multiple independent light sources allows the procedure to be performed via electronic scanning rather than mechanical scanning of the treatment light. Electronic scanning of the treatment light implies that the independent light sources are switched on an off electronically to deliver the treatment rather than mechanically moving a probe or mirrors to reposition the treatment light about the eye. The electronic scanning may provide more consistent, reliable, and safer treatment applications that are less dependent on a health care professional (HCP) and/or mechanical components for precise alignment and control of a treatment beam of light.

According to one aspect, a handheld device for delivering therapeutic light toward an eye of a patient includes a device housing that is configured to be held by a user in delivering the therapeutic light. The device housing has a proximal end and a distal end opposite the proximal end. A plurality of light sources are disposed within the device housing with each light source being configured to independently deliver a beam of therapeutic light toward the distal end of the device housing. An array of lenses is disposed near the distal end of the device housing. Each lens of the array is aligned with a respective light source of the plurality of light sources so that the beam of therapeutic light that is delivered from the respective light source is directed by the respective lens of the array to target tissue of the eye in order to therapeutically treat to the target tissue.

The handheld device may include a control unit that is coupled with the plurality of light sources and that is configured to independently control each light source to switch each light source on and off in therapeutically treating the target tissue. In some embodiments, the control unit may be configured to switch each light source on and off in a sequential manner so that the therapeutic light is delivered sequentially among a plurality of target locations in a clockwise or counterclockwise manner. In other embodiments, the control unit may be configured to switch the light sources on and off so that the therapeutic light is delivered in a sweeping motion across the target tissue of the eye.

The handheld device may also include an infrared camera that is configured to produce an observable spot on the target tissue of the eye by reflecting the beam of therapeutic light off the target tissue. The beam of therapeutic light is delivered from at least one light source of the plurality of light sources and is delivered at an eye safe power level of less than 1 mW. In some embodiments, the beam of therapeutic light may be delivered from each of the light sources at the eye safe power level in order to produce a plurality of observable spots that are used to properly align the beams about the eye.

The handheld device may further include a contact tip having a proximal end and a distal end. The proximal end of the contact tip being detachably coupled with the distal end of the device housing and the distal end of the contact tip comprising a contact surface that is positionable on a surface of the eye. The array of lenses may be disposed within the contact tip. The array of lenses may be arranged within the contact tip so that the array of lenses encircles a limbus of the eye and so that each lens of the array is positioned radially outward of the limbus.

The plurality of light sources may include vertical cavity surface emitting lasers (VCSELs), surface emitting LEDs, or a combination thereof. One or more batteries may be disposed or positioned within the housing so that the handheld device is a self-contained single use disposable unit. The handheld device may include between 10 and 50 individual light sources and lenses, and in a specific embodiment may include 20 individual light sources and lenses.

According to another aspect, a device for providing a therapeutic treatment to an eye includes a housing having a proximal end and a distal end. The housing is configured to be grasped by a user in delivering the therapeutic treatment. An array of lenses is disposed near the distal end of the housing body with each lens of the array being aligned with a beam of therapeutic light provided by a respective light source of a plurality of light sources. Each lens of the array is configured to direct the beam of therapeutic light to target tissue of the eye in order to provide the therapeutic treatment. A control unit is operably coupled with the plurality of light sources and is configured to independently control each light source in order to independently deliver the therapeutic light from each light source to deliver the therapeutic treatment to the target tissue of the eye in an automated fashion.

In some embodiments, the plurality of light sources are disposed within the housing. In other embodiments, the proximal end of the housing may be coupled with an external light source that houses the plurality of light sources. The device may also include an infrared camera that is configured to produce an observable spot on the target tissue of the eye by reflection of the beam of therapeutic light from the target tissue. The beam of therapeutic light may be delivered from at least one light source of the plurality of light sources, typically at an eye safe power level of less than 1 mW.

The device may further include a contact tip having a proximal end and a distal end. The proximal end of the contact tip may be coupled with the distal end of the housing and the distal end of the contact tip may be configured for positioning on a surface of the eye. The array of lenses may be disposed within the contact tip. The contact tip may be removable from the distal end of the housing. The distal end of the contact tip may be curved to correspond with a contour of eye so that the therapeutic light that exits the distal end of the contact tip enters the eye at an angle that is relatively normal to the surface of the eye. The array of lenses may be arranged so that when the contact tip is positioned on the eye, the therapeutic treatment is provided to the eye without requiring a repositioning of the contact tip relative to the eye. The array of lenses may be arranged so that a respective beam of therapeutic light that is delivered from each lens is disposed radially outward of a limbus of the eye. The control unit may be configured to deliver the therapeutic light from each light source in a sequential manner so that therapeutic light is delivered to the target tissue of the eye in a clockwise or counterclockwise manner around the limbus.

According to another aspect, a method for treating an eye includes positioning a contact tip of a handheld treatment device on a surface of the eye, in which the handheld treatment device includes: a device housing; an array of lenses disposed near a distal end of the device housing with each lens of the array being aligned with a beam of therapeutic light that is provided by a respective light source of a plurality of light sources; the contact tip coupled with the distal end of the device housing; and a control unit that is operably coupled with the plurality of light sources and that is configured to independently control each light source to independently deliver the beam of therapeutic light from each light source. The method also includes aligning the contact tip relative to the eye so that the beam of therapeutic light from each respective light source is deliverable to target tissue of the eye to be treated and activating the control unit in order to deliver the beam of therapeutic light from each respective light source in an automated fashion and to direct, via each lens of the array, the beam of therapeutic light from each respective light source to the target tissue to therapeutically treat the target tissue.

The method may further include observing, via an infrared camera, a spot on the target tissue of the eye by reflecting the beam of therapeutic light from the target tissue. The beam of therapeutic light may be delivered from at least one light source of the plurality of light sources and may be delivered at an eye safe power level of less than 1 mW. Delivering the beam of therapeutic light from each respective light source in the automated fashion may include independently delivering the beam of therapeutic light from each light source in a sequential manner so that therapeutic light is delivered to the target tissue of the eye in a clockwise or counterclockwise manner. The therapeutic light may be delivered in a circular pattern around a limbus of the eye. The beam of therapeutic light from each respective light source may be delivered in a series of pulses with each pulse of therapeutic light being sufficient to induce therapeutic healing of the target tissue without damaging the tissue. In some embodiments, delivering the beam of therapeutic light from each respective light source in the automated fashion may include delivering the beam of therapeutic light from each light source in a manner so that therapeutic light is delivered to the target tissue in a sweeping manner.

Embodiments of the disclosure covered by this patent are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

BRIEF DESCRIPTION OF THE DRAWINGS

Further details, aspects, and embodiments of the disclosure will be described by way of example only and with reference to the drawings. In the drawings, like reference numbers are used to identify like or functionally similar elements. Elements in the figures are illustrated for simplicity and clarity and have not necessarily been drawn to scale.

FIGS. 6 & 7 illustrate exemplary treatment procedures that may be employed to treat the eye.

FIG. 8 illustrates exemplary laser parameters for treating an eye according to some embodiments.

FIG. 9 illustrates an embodiment of a contact tip of the ophthalmic treatment device.

DETAILED DESCRIPTION OF THE DISCLOSURE

Figure 1A:
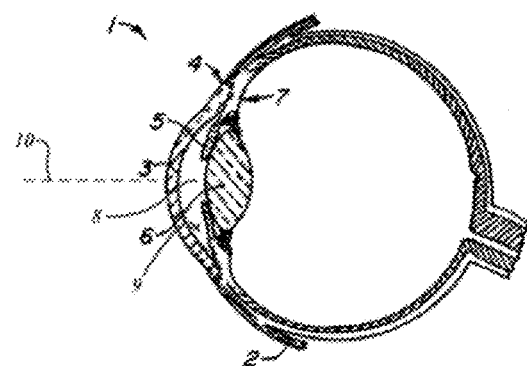
FIG. 1A shows the anatomy of an eye with relevant parts labeled to provide anatomical references.

Conventional ophthalmic laser systems generally require a laser console and a laser probe where the laser console contains the laser source, power supply, and controller. The laser probe generally contains an optical fiber and connector for attachment to the laser console. The laser console is typically an AC powered system, placed on a surface that is at least several feet away from a patient's eye, and the laser output light from the console is typically carried by an optical fiber (i.e., waveguide) to the patient's eye where photocoagulation based treatment may take place. Such a system typically requires external AC power, a long multi-mode fiber to bring light to the end applicator that could be implemented with a slit lamp adapter, a scanner, or a handheld contact probe.

Conventional ophthalmic laser systems also generally employ a single laser or light source. The treatment light that is provided by the single laser source is delivered to the laser probe via the optical fiber. In order to deliver the laser light to the eye tissue the ophthalmic laser system typically requires components (e.g., collimators, lenses, mirrors, and the like) that align and/or redirect the laser beam relative to the eye. Conventional systems also typically require that the laser probe be manually moved relative to the eye to reposition the laser beam at different target or treatment locations about the eye. Manually moving the laser probe over the surface of the eye may be prone to issues such as scratching the eye's surface. In addition, it is difficult to precisely control the location and/or positioning of the probe about the eye and thus, it is difficult to precisely control the delivery the laser light to the eye, which may lead to inconsistent treatment.

The embodiments described herein may provide certain advantages and improvements over conventional ophthalmic laser systems. For example, the ophthalmic laser system described herein does not include a traditional laser console. Instead, the treatment probe may be configured to house the treatment light source within the probe handle. Additionally, in some embodiments, the handheld treatment probe may include a user interface, such as dials and buttons, for adjusting various parameters of the therapeutic light. With certain embodiments, the self-contained handheld treatment probe may be operated independent of an AC power source. For example, in some embodiments, the handheld treatment probe may be battery powered. Additionally, the handheld treatment probe may be disposable or may utilize replaceable distal tips. Many embodiments may be particularly designed for transscleral cyclophotocoagulation where energy is directed through selected portions of the pars *plicata* region to the ciliary body, structures under the scleral layers, and the overlying conjunctiva to treat a glaucomatous eye.

In addition, the embodiments described herein minimize or eliminate issues associated with manually moving the laser probe about the eye by employing an array of lenses that deliver therapeutic light to a plurality of treatment locations about the eye. The array of lenses allow the therapeutic light to be delivered to the eye without requiring movement of a laser probe. Stated differently, the laser probe may be maintained stationary or in position on the eye while the array of lenses delivers the therapeutic light to multiple target or treatment positions about the eye. In some embodiments, the array of lenses may be embodied in a contact tip that is attached to a distal end of a laser probe. The contact tip may be a single use device or a multi-use device as desired. The contact tip may have a cup shaped distal end that matches the contour of the patient's eye. The array of lenses may define and enable automated cyclo-scanning of the therapeutic light using a laser or LED device. Additional features and aspects of the embodiments will be more apparent in reference to the various figures described herein below.

FIG. 1A shows the anatomy of an eye 1 with relevant parts labeled to provide anatomical references. The sclera 2 is a tough sheath around the eye which meets the cornea 3 at a circular junction called the limbus 4. Behind the cornea 3 lies the iris 5, the lens 6 and the ciliary body and related processes 7. The anterior chamber is the fluid-filled compartment within the eye 1 just in front of the pupil 8. Viewed in profile, the anterior chamber is bounded by the domed cornea 3 in front and by the colored iris 5 behind. Where the cornea 3 and the iris 5 converge they form an angle 9 referred to herein as the angle of the anterior chamber. Further eye 1 may have a visual/optical axis 10.

Figure 1B:
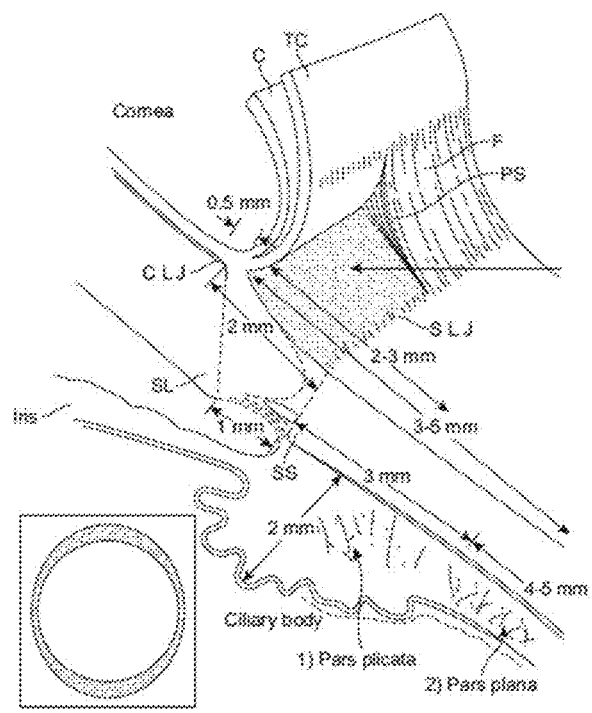
FIG. 1B shows further details of the eye anatomy.

FIG. 1B shows further details of the surgical eye anatomy. Embodiments described herein may target intraocular structures (also referred to herein as target tissue) that span from the posterior pars plicata to the pars plana. Alternatively, the pars plana may be targeted and the pars plicata, ciliary body, and other ciliary processes avoided.

Figure 2:
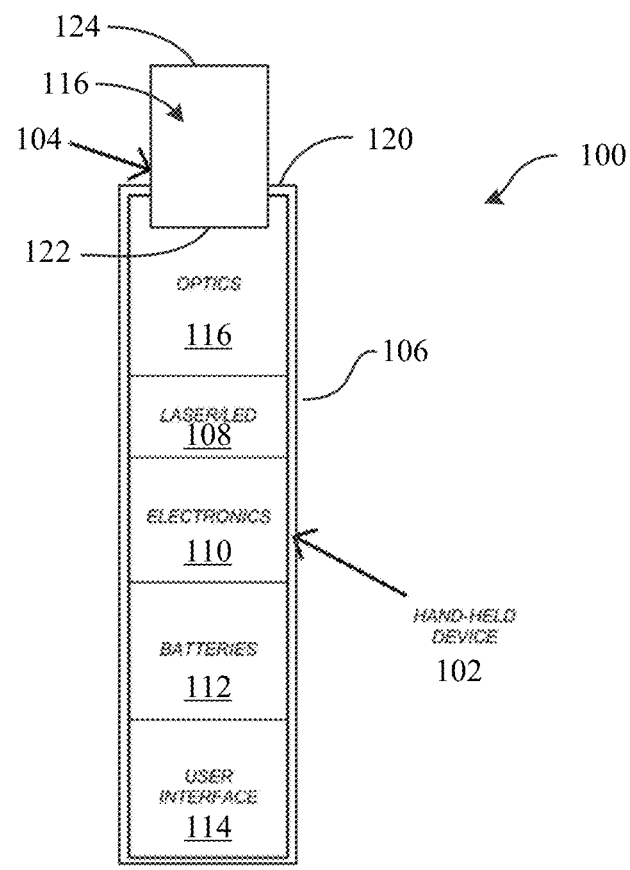
FIG. 2 illustrates an exemplary ophthalmic treatment device according to some embodiments of the disclosure.

FIG. 2 illustrates an exemplary ophthalmic treatment device 100 that may be used to target the ciliary body and/or pars plana. The ophthalmic treatment device 100 has a treatment device body 102 and a replaceable, single-use or multi-use tip 104 that is detachably coupled with the treatment device body 102. The treatment device body 102 includes a housing 106 with an exterior surface that defines a handle for grasping by a user. The treatment device body 102 may include a therapeutic light source assembly or array 108 that is configured to provide therapeutic light for treatment of the target tissue of the eye. As described herein, the light source assembly 108 typically includes a plurality of light sources with each light source being configured to independently deliver therapeutic light for treatment of the target tissue of the eye. The light source assembly 108 is typically positioned within the housing 106, although in some embodiments, the proximal end of the housing 106 may couple with an external light source that houses the light source assembly 108.

The treatment device body 108 also includes lens array optics 116, which is an array or ring of lenses as described herein. Each lens of the array of lenses is aligned with one of the light sources and is configured to direct a beam of therapeutic light to the target tissue. As illustrated in FIG. 2, in some embodiments the lens array optics 116 may be positioned within the housing 106 while in other embodiments the lens array optics 116 may be part of the single-use or multi-use tip 104 (also referred to herein as a contact tip 104). In yet other embodiments, the lens array optics 116 may be split between the housing 106 and the single-use or multi-use tip 104. The light source assembly 108 is operably coupled or associated with a control unit or electronics 110. The treatment device body 102 may also include one or more batteries 112 and/or a user interface 114.

Figure 3:
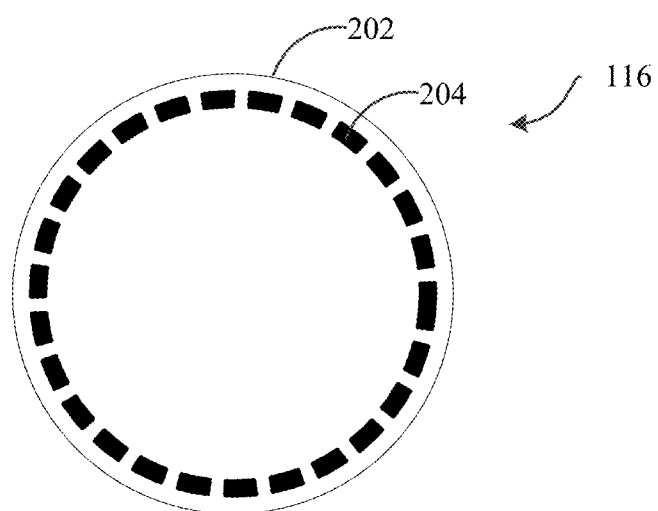
FIG. 3 illustrates a schematic drawing of lens array optics of the ophthalmic treatment device.

FIG. 3 illustrates a schematic drawing of the lens array optics 116 of the ophthalmic treatment device 100. The lens array optics 116 include an array of lenses 204 that are positioned about a single optic medium or body 202. In an exemplary embodiment, the array of lenses 204 is arranged about the single optic medium or body 202 so that the array of lenses 204 for a ring shaped curve around the medium or body 202. The ring shaped array of lenses may be used to direct treatment light around the limbus of the eye. The medium or body 202 is positioned near the distal end of the housing 106 and may be enclosed within the housing 106, or may more commonly may be positioned within the single-use or multi-use tip 104. In a specific embodiment, the medium or body 202 is the body of the contact tip 104 described herein so that the contact tip 104 and lens array optics 116 is a single component. The array of lenses 204 are positioned near a circumferential or peripheral edge of the optic medium or body 202 and may be arranged so that when the treatment device body 102 is positioned on a patient's eye, each lens 204 of the array is positioned radially outward from the limbus of the eye. The array of lenses 204 surround the eye to be treated in an arrangement that is typical for the cyclophotocoagulation. This configuration ensures that the treatment light will be delivered to target tissue rather than to other tissue of the eye, such as the iris.

The optic medium or body 202 may be made of a glass lens, a plastic lens, or of any other material employed in forming optic media. The individual lenses 204 are embedded in the single optic medium or body 202 so that each lens 202 aligns with a light source of the light source assembly 108 (see FIG. 5). The alignment of each lens 202 with a respective light source of the light source assembly 108 enables the beam of therapeutic light that is delivered from the respective light source to be directed by the respective lens to the target tissue of the eye in order to therapeutically treat the target tissue. The array of lenses 204 many include two or more individual lenses, but more commonly includes 10 or more lenses. In other embodiments, the array of lenses 204 includes between 10 and 50 lenses, and in a specific embodiment, the array of lenses 204 nominally includes 20 individual lenses.

Figure 4:
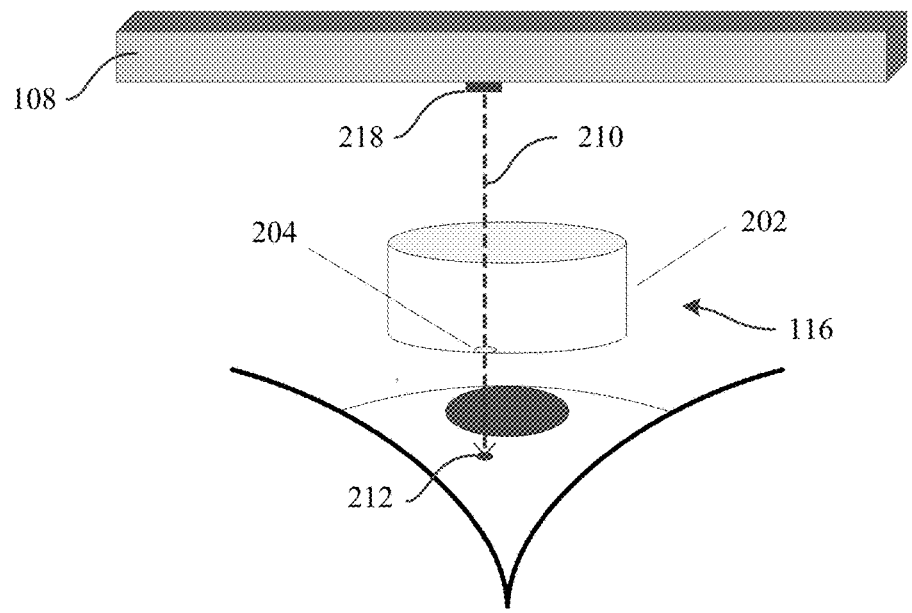
FIGS. 4 & 5 illustrate representations of the lens array optics being used with a light source assembly to deliver therapeutic light to target tissue of the eye.
Figure 5:
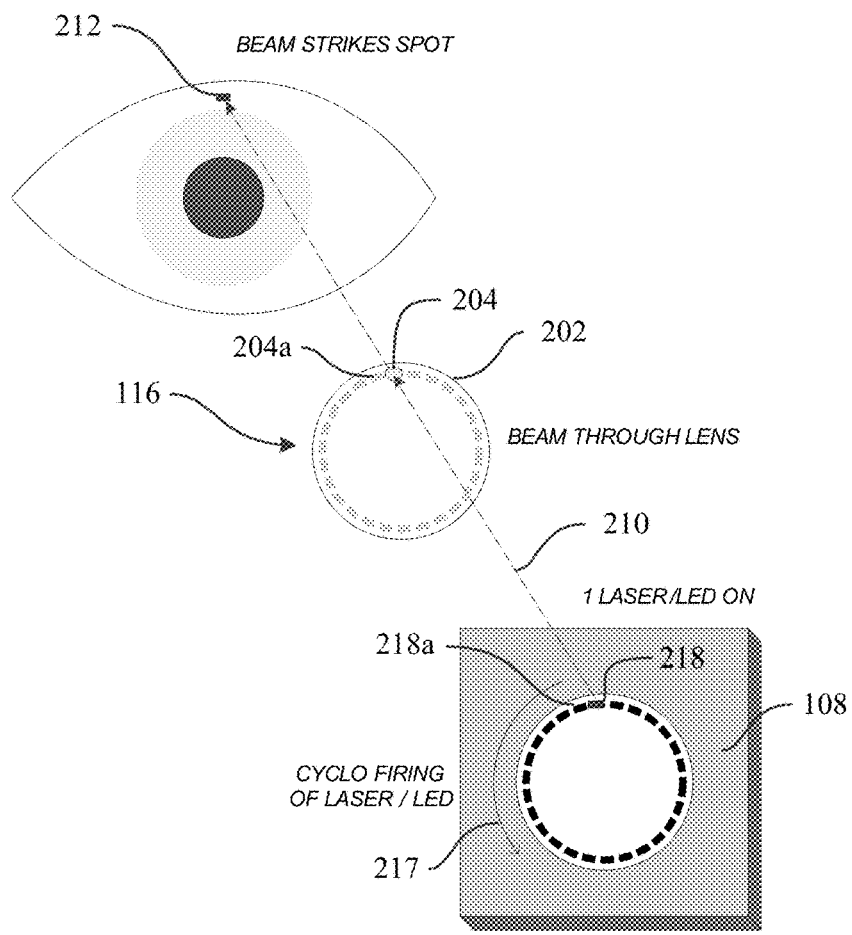

FIGS. 4 and 5 illustrate representations of the lens array optics 116 being used with the light source assembly 108 to deliver therapeutic light 210 to target tissue 212 of the eye. FIG. 5 shows the light source assembly 108 including an array of independent or individual light sources 218 that are used in delivering therapeutic light 210 to the target tissue 212 of the eye. Reference numeral 218 is used herein to represent both an individual light source and the array of light sources. Reference numeral 204 is similarly used herein to represent both an individual lens and the array of lenses. Typically the light source assembly 108 is coaxially aligned with the lens array optics 116 and the eye. These components are illustrated in FIG. 5 out of axial alignment to illustrate the interaction of the components in delivering the therapeutic treatment to the target tissue 212.

Figure 10:
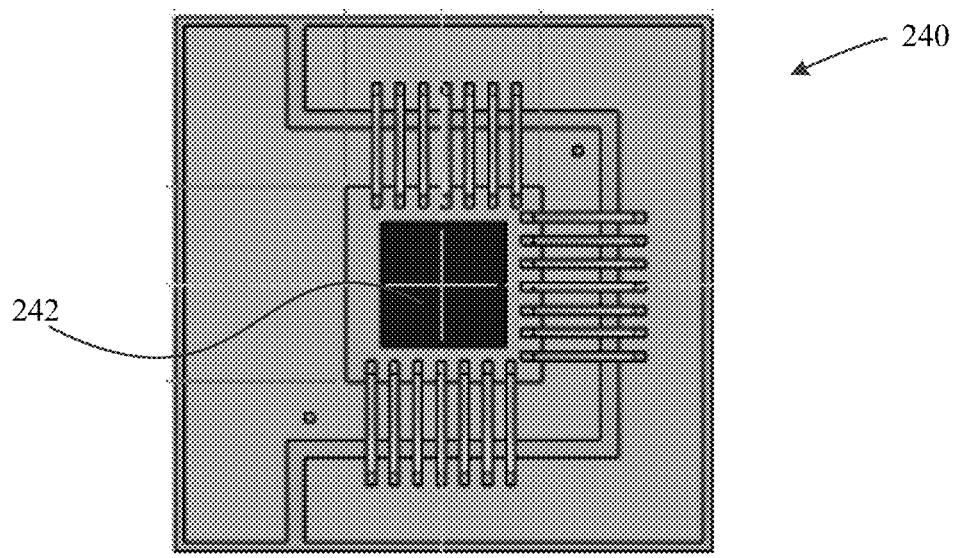
FIG. 10 illustrates a surface emitting laser diode that may be used as a light source in the ophthalmic treatment device.

In an exemplary embodiment, each light source 218 is a vertical cavity surface emitting lasers (VCSELs) or a surface emitting LED, or a combination thereof. A VCSEL laser emits a single mode beam that is significantly simpler to align with an individual lens than edge emitting lasers or other conventional lasers. FIG. 10 illustrates a surface emitting laser diode 240 that may be used in the light source assembly 108. The surface emitting laser diode 240 includes a surface emitting laser 242 that emits a circular beam. In a specific embodiment, each light source 218 may be configured to deliver 1-10 watt 810 nm laser light, which is a light source that is significantly less expensive than those employed in conventional laser treatment probes. A typical VCSEL made with the GaAs/AlGaAs compound semiconductor material could have a lasing wavelength of 780-860 nm depending on the aluminum content and the vertical cavity length.

The use of a VCSELs or surfacing emitting LED provides several advantages over edge emitting lasers that are used in conventional devices. For example, VCSELs emit a symmetric, circular beam that is typically contained in an angle of approximately 15 degrees. Such a beam can be easily collimated onto a circular spot with lower cost lenses. In contrast, edge emitting laser diodes emit a far field beam that is not symmetric and requires the use of special collimators, diodes, and various other components for shaping and aligning the beam with optic fibers and/or other components. Such collimation is difficult to control since the focal length of the fast axis and slow axis require different lens designs. The ophthalmic treatment device 100 of the instant application does not require the use of any optical fibers and thus, the system may be entirely free of optical fibers and the components that are associated therewith.

In FIGS. 4 and 5, the lens array optics 116 is aligned with the light source assembly 108 so that a beam of therapeutic light 210 that is emitted by an individual light source 218 is focused through an individual lens 204 of the lens array and directed onto the target tissue 212 of the eye to be treated. After the target tissue 212 is treated, the individual light source 218 is switched off and another individual light source (e.g., 218a) is switched on in order to emit another beam of therapeutic light (not shown) that is focused by another individual lens 204a and directed onto other target tissue (not numbered) of the eye. Each of the individual light sources of the light source array are similarly individually controlled to sequentially fire or emit a respective beam of therapeutic light that is focused by a corresponding lens of the lens array and directed onto target tissue of the eye at different locations. The sequential delivery of a beam of therapeutic light from the individual light sources 218 and individual lenses 204 to the eye allows the ophthalmic treatment device 100 to remain stationary about the eye while individual target tissue locations are treated with the therapeutic light. The use of the light source array and the lens array also allows the sequential delivery of therapeutic light to be achieved without requiring the ophthalmic treatment device 100 to include any moving parts that redirect the beam of therapeutic light. The ophthalmic treatment device 100 of the instant disclosure employs electronic scanning of the treatment beam rather than mechanical scanning, which is typically less expensive to manufacture, easier to implement or program, and less prone to failure or other associated issues. The use of multiple laser light sources also make the system more redundant and less vulnerable to a single failure point, such as an individual light source. In addition, the ophthalmic treatment device 100 of the instant disclosure does not require an optical waveguide or probe to focus the therapeutic light on the front of the eye.

Although the individual light sources 218 are described as being individually controlled to emit a beam of therapeutic light, it should be realized that in other embodiments, multiple individual light sources 218 may be simultaneously controlled or switched on to simultaneously deliver multiple beams of therapeutic light.

The array of light sources 218 is mounted on a device that is placed a distance from the eye. The array of light sources 218 is typically disposed within the housing 106, but may be positioned elsewhere as required or desired. The number of individual light sources 218 is typically similar to the number of target sites to be treated. In an exemplary embodiment 20 individual light sources are employed. Likewise, the number of individual lenses 204 is similar to the number of individual light sources 218, which in the exemplary embodiment is 20 individual lenses.

The control unit 110 is operably coupled with the individual light sources 218 to individually control and power on the light sources 218 in a desired manner. For example, the control unit 110 may power on the light sources 218 so that a treatment beam of light travels around the eye in a clockwise or counterclockwise direction 217. In this manner, the light source assembly 108 and lens array optics 116 may be employed in delivering a desired therapeutic treatment, such as cyclophotocoagulation. The control unit 110 may likewise be programmed to deliver other treatment patterns or procedures.

As described herein, the lens array optics 116 may be part of the contact tip 104, which may be a single-use or multi-use component. The contact tip 104 may have a cup shaped arrangement that is configured to be directly pressed against the treated eye. The contact tip 104 may be designed with a usage recording device that may include one or more of the following devices: an RFID, a memory chip, a special mechanical attachment mechanism (locking, keys, etc.), and/or an electronic reader attached to the laser/LED source. A distal end 124 of the contact tip 104 is positioned against the sclera 2 of the eye 1 and the ophthalmic treatment device 100 may be held parallel to the visual axis 10 of the eye 1. The ophthalmic treatment device 100 is then able to apply energy to a plurality of spaced apart fixed locations via the light source assembly 108 and lens array optics 116 as described above.

FIGS. 6 and 7 illustrate exemplary treatment procedures that may be employed to treat the eye. The ophthalmic treatment device 100 may be used to deliver therapeutic light to target tissue of the eye in a variety of different methods. For example, U.S. Patent Publication 2010/0076419, incorporated herein by reference in its entirety, describes a method of delivering energy toward target tissues at a plurality of spaced apart fixed locations. FIG. 6 illustrates the plurality of spaced apart fixed locations 117 about the limbus 4 of the eye that are each treated with therapeutic light. In the conventional treatment, the laser probe is moved and repositioned about the eye in order to treat each spaced apart fixed location 117. In contrast to the conventional procedures, the ophthalmic treatment device 100 described herein is able to treat each spaced apart fixed location 117 while the ophthalmic treatment device 100 remains stationary about the eye. This is due to the use of the light source assembly 108 and lens array optics 116 that include a plurality of independent or individual light sources and corresponding lenses. The spaced apart fixed location 117 correspond to the individual light sources 218 and lenses 204. The ophthalmic treatment device 100 is able to treat each location of the spaced apart fixed locations 117 by individually firing a beam of therapeutic light from the individual light sources, which is focused and directed onto the respective target tissue from the individual lenses. In delivering the treatment, the therapeutic light may be delivered once to each spaced apart fixed location 117, or may be delivered multiple times to each spaced apart fixed location 117. For example, the therapeutic light may be cycled clockwise or counterclockwise a single time around the eye to each spaced apart fixed location 117, or the therapeutic light may be cycled clockwise or counterclockwise multiple times around the eye to each spaced apart fixed location 117.

FIG. 7 illustrates another treatment method where a treatment probe is slid or swept across the target tissue concurrently with the light delivery. This treatment method is further described in U.S. Patent Publication 2015/0374539, which is incorporated herein by reference in its entirety. The ophthalmic treatment device 100 described herein is able to mimic the treatment method illustrated in FIG. 7 by controlling the individual light sources so that treatment beam is moved back and forth across the eye in a sweeping or sliding type motion. This motion of the treatment beam is achieved without requiring movement or repositioning of the ophthalmic treatment device 100 due to the inclusion of the individual light sources and lens array. The ophthalmic treatment device 100 may likewise be used to provide other treatment procedures.

As briefly described above, the control unit 110 is operably coupled with and configured to independently control the individual light sources 218 by switching each light source on or off in an automated fashion. The control unit 110 may switch each light source 218 on and off in a sequential manner so that therapeutic light is delivered sequentially among a plurality of target locations in a clockwise or counterclockwise manner around the limbus as shown in FIG. 6, the control unit 110 may switch the light sources 218 on and off so that therapeutic light is delivered in a sweeping motion across the tissue of the eye as shown in FIG. 7, or the control unit 110 may switch the light sources 218 on and off in another manner to deliver a different desired therapeutic treatment. The control unit 110 may include a laser driver board and a software/firmware controller to independently control each light source.

In certain embodiments, the light source assembly 108 and control unit 110 may be configured to deliver light energy in a pulsed or continuous wave emission mode. Careful selection of the laser energy pulse "on" and "off" times can avoid undesired thermal damage to a target by allowing the target to cool during the "off" time of the laser before the next pulse of energy is delivered during the "on" time. The duty cycle may be selected so that cumulative thermal buildup, caused by insufficient cooling during the "off" time may be avoided. Thus, damage may be reduced to a minimum level sufficient to trigger a biological response needed for lowering of intraocular pressure (IOP). FIG. 8 illustrates an exemplary pulsed mode that may be used in some embodiments of the present invention. The illustrated mode may have an "on" time of 100 µs and an "off" time of 1900 µs with a period of 2000 µs.

In typical embodiments, a semiconductor laser diode or a semiconductor laser diode pumped laser (e.g., DPSS green/yellow laser) is used as the light source for ophthalmic therapy. Such lasers have defined peak lasing wavelengths such as 532 nm, 577 nm or 810 nm, and have defined spectral line width such as +/−3 nm, and have defined threshold current such as 700 mA for an 810 nm laser diode, and have defined electrical impedances that allow the lasers to be electrically or optically modulated at any repetition rate (such as 1 kHz or higher), with pulse width at any value (such as 1 ns or higher), for an extended period of time (such as 1 ms or longer).

The light source in the embodiments could be a single mode laser, a multimode laser, or a broad spectrum LED such as a visible spectrum LED for different colors (e.g., green, yellow, or red). The pulse energy, pulse width and pulse repetition rate (aka duty cycle) can be adjusted to provide optimum treatment effect such as demonstrated by the MicroPulse© laser treatment parameters.

Electronics 110 may further include a feedback control implemented in hardware to control the light source assembly 108 power that is faster than the response of a software control loop. The hardware optical power feedback control is preferably implemented with a commercially available laser driver chip that has built-in automatic power control feature that uses photodetector input that correlates with laser output to directly control the bias current of the laser diode to achieve constant power level. This typically results in fast real time power control when compared with a software feedback loop.

In some embodiments, batteries 112 can be an alkaline battery, lead-acid battery, lithium-ion battery, or any other rechargeable or disposable battery. The treatment device body 102 may include a battery receptacle for receiving the battery 112 and the housing 106 may include a removable cover for battery 112 replacement when needed. The use of a battery 112 to power a therapeutic light source assembly 108 housed in the same housing 106 may allow for more convenient treatments as the ophthalmic treatment device 100 may not need to be tethered to a separate laser console. The lack of tethering to a laser console may also allow for a greater freedom of motion with the ophthalmic treatment device 100 and better targeting of tissues. Additionally, the battery powered ophthalmic treatment device 100 may allow for the use of the ophthalmic treatment device 100 in rural or secluded areas where electricity is not available. Additionally, the ophthalmic treatment device 100 housing the light source assembly 108 and the power source 112 may potentially reduce manufacturing costs which may allow for greater availability of ophthalmic treatment device 100 in emerging markets.

User interface 114 may comprise one or more mechanical dials, buttons, or switches that may be used to adjust parameters of the therapeutic light source with or without a touchscreen or a dedicated electronic display. When a non-touch-screen user interface is employed, a simple mechanical display using digits to indicate laser settings may be used. Additionally or alternatively, treatment parameters may be communicated to the probe via radio frequency, such as Bluetooth.

The user interface 114 may also comprise an infrared camera that is used to observe the 810 nm infrared laser beam at a standby power level such as less than 1 mW (eye safe) when the beam spot incident on the eye tissue is reflected back to the infrared camera and is observable to the laser operator. The observed low power laser spot can be used as the aiming beam, similar to that which is usually implemented with a different wavelength (e.g., 650 nm red laser diode), but in this embodiment the aiming beam is produced by the same treatment beam at an eye-safe level (i.e., <1 mW). This aiming beam would represent the true beam spot for the treatment laser beam, which is more precise than an auxiliary aiming beam from a separate laser diode that is not always coaxially aligned with the treatment beam.

In some embodiments, the housing 106 may optionally include an illumination light source. The illumination light source may be configured to direct white light into the eye to illuminate the ciliary process, as described in U.S. Patent Publication 2015/0305938, incorporated by reference herein in its entirety. The illuminated tissue may help a clinician align of the probe 100 with the tissue during therapeutic light delivery.

FIG. 9 illustrates an embodiment of the contact tip 104. Although the contact tip 104 may be a single-use component or a multi-use component, in an exemplary embodiment, the contact tip 104 is a single-use component that is removable from the housing 106 and is and replaceable with another contact tip 104. The contact tip 104 separates the light source and the distal end of the ophthalmic treatment device 100, which may be hot, from the surface of the eye to ensure that the surface of the eye is not damaged. In an exemplary embodiment, the contact tip 104 is the medium or body 202 illustrated in FIG. 3, which may be made of a glass lens, a plastic lens, or of any other material employed in forming optics. The contact tip 104 may be a hollow of solid body of material as desired.

The contact tip 104 includes a proximal end 122 and a distal applicator end 124 opposite the proximal end 122. The contact tip 104 also typically houses or includes the lens array optics 116. Specifically, the lens array is often integrally formed with or otherwise attached to the contact tip 104. The contact tip 104 may be designed to produce a certain spot size of the therapeutic light on the target tissue. The spot size of the therapeutic light may be adjusted by selecting a different contact tip 104 to use for the treatment procedure. The lens array is typically arranged in a ring shape pattern within the contact tip 104 so that the array of lenses encircles the limbus of the eye and so that each lens of the array is positioned radially outward of the limbus.

The proximal end 122 of the contact tip 104 is configured to mechanically couple with the distal end 120 of the housing 106 of using one or more engagement features. For example, FIG. 9 illustrates the proximal end 122 of the contact tip 104 having a threaded engagement feature 194 that allows the contact tip 104 to be rotatably engaged and disengaged with the housing 106, which may include a corresponding threaded engagement feature. The contact tip 104 may alternatively include one or more protrusions (not shown) that snap fit within one or more corresponding engagement features of the housing 106, or may include any other male or female connector that engages with a corresponding female or male connector of the housing 106.

Since the distal end 124 of the contact tip 104 is typically positioned against the eye, a contact surface 196 of the distal end 124 is typically contoured to match the contour of the eye. For example, the contact surface 196 may be concave with a curvature configured to match the curvature of the sclera. The concave configuration of the contact surface 196 may render the contact surface essentially cup shaped with a configuration that corresponds to an average eye geometry. The contoured configuration of the contact surface 196 may also ensure that the beam of therapeutic light is delivered at an angle that is normal to the surface of the eye. The contact tip 104 may also be keyed to ensure a proper alignment of the contact tip 104 and housing 106. The keyed configuration of the contact tip 104 may help ensure that the lens array is properly aligned with the light source array so that each beam of therapeutic light properly aligns with, and is focused by, a corresponding lens. The keyed contact tips 104 may also facilitate in replacement of the tip with the lens array and light source array axially aligned.

In some embodiments, the contact tip 104 includes a computer readable media. The computer readable media may be an optical barcode (e.g., 2D barcode), embedded chip (e.g., RFID, NFC, direct read memory chip), and the like. The computer readable media may be read by a corresponding sensor associated with the treatment device body 102. In some embodiments, the computer readable media may be a security feature that protects the treatment device body 102 from being used with unauthorized replacement contact tips 104. Optionally, the computer readable media may carry treatment parameter information associated with the contact tip 104. For example, a contact tip 104 may be coupled with the treatment device body 102 and a sensor of the treatment device body may read the computer readable media to determine which treatment parameters are associated with the type of contact tip 104 that is attached thereto. Thereafter, the control unit 110 of the treatment device body 102 may be configured to automatically adjust parameters of the light source assembly 108 for the particular treatment.

As described above, an infrared camera can optionally be included in the user interface 114 to observe the laser treatment beam at an eye safe level (i.e., <1 mW). In such embodiments, the beam spot may be used to guide the treatment laser beam when it is fired at higher power levels.

Figure 11:
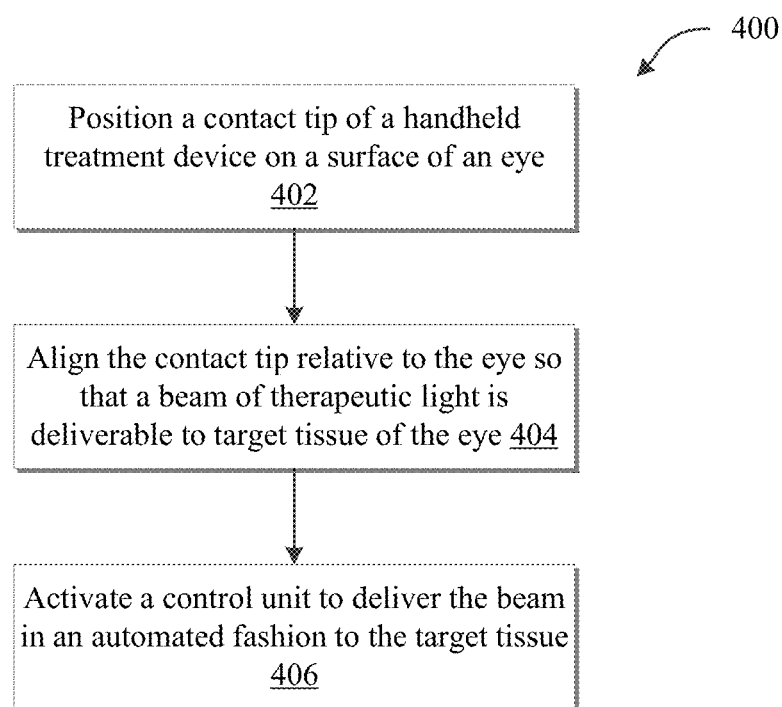
FIG. 11 illustrates a method for treating an eye.

FIG. 11 illustrates a method 400 for treating an eye. At block 402, a contact tip of a handheld treatment device is positioned on a surface of the eye. As described herein, the handheld treatment device includes a device housing, an array of lenses, the contact tip, and a control unit. The array of lenses is disposed near a distal end of the device housing and each lens of the array is aligned with a beam of therapeutic light that is provided by a respective light source of a plurality of light sources. The contact tip is coupled with the distal end of the device housing and the control unit is operably coupled with the plurality of light sources. The control unit is configured to independently control each light source to independently deliver the beam of therapeutic light from each light source.

At block 404, the contact tip is aligned relative to the eye so that the beam of therapeutic light from each respective light source is deliverable to target tissue of the eye to be treated. At block 406, the control unit is activated in order to deliver the beam of therapeutic light from each respective light source in an automated fashion and to direct, via each lens of the array, the beam of therapeutic light from each respective light source to the target tissue to therapeutically treat the target tissue.

In one embodiment, delivering the beam of therapeutic light from each respective light source in the automated fashion comprises independently delivering the beam of therapeutic light from each light source in a sequential manner so that therapeutic light is delivered to the target tissue of the eye in a clockwise or counterclockwise manner. In such an embodiment, the therapeutic light may be delivered in a circular pattern around a limbus of the eye. The beam of therapeutic light from each respective light source may be delivered in a series of pulses with each pulse of therapeutic light being sufficient to induce therapeutic healing of the target tissue without damaging the tissue. In another embodiment, delivering the beam of therapeutic light from each respective light source in the automated fashion may include delivering the beam of therapeutic light from each light source in a manner so that therapeutic light is delivered to the target tissue in a sweeping manner.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of treating an eye of a patient using a plurality of light sources, the method comprising:
    positioning a contact tip of a treatment device on a surface of the eye, the treatment device comprising:
        a device housing;
        an array of lenses disposed near a distal end of the device housing, each lens of the array of lenses being aligned with a beam of therapeutic light that is provided by a respective light source of the plurality of light sources; and
        a control unit that is operably coupled with the plurality of light sources and that is configured to independently control each light source to independently deliver the beam of therapeutic light from each respective light source;
    aligning the contact tip relative to the eye so that the beam of therapeutic light from each respective light source is deliverable to target tissue of the eye to be treated; and
    activating the control unit in order to deliver the beam of therapeutic light from each respective light source in an automated fashion and to direct, via each lens of the array of lenses, the beam of therapeutic light from each respective light source to the target tissue to treat the eye;
    wherein the beam of therapeutic light is delivered to the target tissue to treat glaucoma.

2. The method of claim 1, further comprising observing, via an infrared camera, a spot on the target tissue of the eye by reflecting the beam of therapeutic light from the target tissue, the beam of therapeutic light being delivered from at least one light source of the plurality of light sources and being delivered at a power level of less than 1 mW.

3. The method of claim 1, wherein delivering the beam of therapeutic light from each respective light source in the automated fashion comprises independently delivering the beam of therapeutic light from each respective light source in a sequential manner so that therapeutic light is delivered to the target tissue of the eye in a clockwise or counter-clockwise manner.

4. The method of claim 3, wherein the therapeutic light is delivered in a circular pattern around a limbus of the eye.

5. The method of claim 4, wherein the beam of therapeutic light from each respective light source is delivered in a series of pulses with each pulse inducing therapeutic healing of the target tissue without damaging the target tissue.

6. The method of claim 4, wherein each lens of the array of lenses is positioned radially outward of the limbus.

7. The method of claim 1, wherein delivering the beam of therapeutic light from each respective light source in the automated fashion comprises delivering the beam of therapeutic light from each light source in a manner so that therapeutic light is delivered to the target tissue in a sweeping manner.

8. The method of claim 1, wherein the array of lenses is disposed within the contact tip.

9. The method of claim 1, wherein the plurality of light sources comprise vertical cavity surface emitting lasers (VCSELs), surface emitting LEDs, a combination thereof.

10. The method of claim 1, wherein the device is a self-contained single use disposable unit, and wherein the method is performed without attaching the device to an external component.

11. A method of treating an eye of a patient, the method comprising:
    positioning a contact tip of a treatment device on a surface of the eye, the treatment device comprising:
        a device housing; and
        an array of lenses disposed near a distal end of the device housing, each lens of the array of lenses being aligned with a beam of therapeutic light that is provided by a light source;
    aligning the contact tip relative to the eye so that the beam of therapeutic light from the light source is deliverable to target tissue of the eye to be treated;
    delivering the beam of therapeutic light from the light source in an automated fashion;
    directing, via each lens of the array of lenses, the beam of therapeutic light from the light source to the target tissue to treat the eye; and
    treating the eye without repositioning the contact tip relative to the eye.

12. The method of claim 11, wherein the treatment device further comprises a control unit that is operably coupled with the light source and that is configured to control the light source to deliver the beam of therapeutic light from the light source, and wherein the method further comprises activating the control unit to deliver the beam of therapeutic light from the light source in an automated fashion and to direct, via each lens of the array of lenses, the beam of therapeutic light from the light source to the target tissue.

13. The method of claim 11, further comprising coupling a proximal end of the device housing with an external light source.

14. The method of claim 11, wherein a distal end of the contact tip is curved such that the beam of therapeutic light exiting the distal end of the contact tip enters the eye at an angle normal to the surface of the eye.

15. The method of claim 11, wherein the beam of therapeutic light is directed, via each lens of the array of lenses, to the target tissue so that the beam of therapeutic light from each lens is disposed radially outward of a limbus of the eye.

16. The method of claim 15, wherein the beam of therapeutic light is delivered a sequential manner clockwise or counterclockwise around the limbus.

17. The method of claim 11, wherein delivering the beam of therapeutic light from the light source comprises independently delivering a respective beam of therapeutic light from the light source in a sequential manner.

18. The method of claim 11, wherein delivering the beam of therapeutic light from the light source comprises delivering a series of pulses of therapeutic light, each pulse inducing therapeutic healing of the target tissue without damaging the target tissue.

19. A method of treating an eye of a patient, the method comprising:
   positioning a contact tip of a treatment device on a surface of the eye, the treatment device comprising:
      a device housing; and
      an array of lenses disposed near a distal end of the device housing, each lens of the array of lenses being aligned with a beam of therapeutic light that is provided by a light source;
   aligning the contact tip relative to the eye so that the beam of therapeutic light from the light source is deliverable to target tissue of the eye to be treated;
   delivering the beam of therapeutic light from the light source in an automated fashion; and
   directing, via each lens of the array of lenses, the beam of therapeutic light from the light source to the target tissue to treat the eye;
   wherein delivering the beam of therapeutic light from the light source comprises delivering a series of pulses of therapeutic light, each pulse inducing therapeutic healing of the target tissue without damaging the target tissue.

20. The method of claim 19, wherein the treatment device further comprises a control unit that is operably coupled with the light source and that is configured to control the light source to deliver the beam of therapeutic light from the light source, and wherein the method further comprises activating the control unit to deliver the beam of therapeutic light from the light source in an automated fashion and to direct, via each lens of the array of lenses, the beam of therapeutic light from the light source to the target tissue.

21. The method of claim 19, further comprising coupling a proximal end of the device housing with an external light source.

22. The method of claim 19, wherein a distal end of the contact tip is curved such that the beam of therapeutic light exiting the distal end of the contact tip enters the eye normal to the surface of the eye.

23. The method of claim 19, further comprising treating the eye without repositioning the contact tip relative to the eye.

24. The method of claim 23, wherein the beam of therapeutic light is directed, via each lens of the array of lenses, to the target tissue so that the beam of therapeutic light from each lens is disposed radially outward of a limbus of the eye.

25. The method of claim 24, wherein the beam of therapeutic light is delivered a sequential manner clockwise or counterclockwise around the limbus.

26. The method of claim 19, wherein delivering the beam of therapeutic light from the light source comprises independently delivering a respective beam of therapeutic light from the light source in a sequential manner.

* * * * *